US010605806B2

(12) United States Patent
Lim et al.

(10) Patent No.: US 10,605,806 B2
(45) Date of Patent: Mar. 31, 2020

(54) ELECTROCHEMICAL IMMUNOSENSOR AND METHOD OF USE FOR ANALYTE DETECTION

(71) Applicants: Syazana Abdullah Lim, Gadong (BN); Minhaz Uddin Ahmed, Jalan (BN)

(72) Inventors: Syazana Abdullah Lim, Gadong (BN); Minhaz Uddin Ahmed, Jalan (BN)

(73) Assignee: Universiti Brunei Darussalam, Gadong (BN)

( * ) Notice: Subject to any disclaimer, the term of this patent is extended or adjusted under 35 U.S.C. 154(b) by 314 days.

(21) Appl. No.: 15/131,438

(22) Filed: Apr. 18, 2016

(65) Prior Publication Data
US 2016/0341722 A1 Nov. 24, 2016

Related U.S. Application Data

(60) Provisional application No. 62/163,906, filed on May 19, 2015.

(51) Int. Cl.
*G01N 33/543* (2006.01)
(52) U.S. Cl.
CPC ..... *G01N 33/5438* (2013.01); *G01N 2333/61* (2013.01)
(58) Field of Classification Search
None
See application file for complete search history.

(56) References Cited

PUBLICATIONS

Lim et al. ("A highly sensitive gold nanoparticle bioprobe based electrochemical immunosensor using screen printed graphene biochip" RSC Adv., 2014, 4, 58460).*
Lim et al. ("A carbon nanofiber-based label free immunosensor for high sensitive detection of recombinant bovine somatotropin" Biosensors and Bioelectronics 70 (2015) 48-53).*
Eissa et al. ("A graphene-based label-free voltammetric immunosensor for sensitive detection of the eggallergen ovalbumin" Analyst, 2013, 138, 4378-4384) (Year: 2013).*
Dervilly-Pinel et al. ("Analytical strategies to detect use of recombinant bovine somatotropin in food-producing animals" Trends in Analytical Chemistry 53 (2014) 1-10). (Year: 2014).*
Ho et al. ("Ultrasensitive electrochemical detection of biotin using electrically addressable site-oriented antibody immobilization usingelectrically addressable site-oriented antibody immobilization approach via aminophenyl boronic acid" Trends in Analytical Chemistry 53 (2014) 1-10). (Year: 2014).*

\* cited by examiner

*Primary Examiner* — Rebecca L Martinez
(74) *Attorney, Agent, or Firm* — Geeta Kadambi; Riddhi IP LLC

(57) ABSTRACT

A carbon nanofiber-based label free electrochemical immunosensor for sensitive detection of proteins in a fluid is described. The immunosensor as disclosed is a modified carbon nano-fiber screen printed electrode (CNF-SPE) wherein the electrode is modified with a carboxyphenyl film and then activated by EDC/NHS. Further, a monolayer of 4-aminophenylboronic acid coating was then fabricated onto the electrode to allow orientation of antibody via bonding of boronic acid-saccharide of oligosaccharide moiety located on the Fc region of antibody. The modified electrode is then used for the detection of a hormone such as rbST in a fluid with a detection limit of 1 pg/ml.

9 Claims, 5 Drawing Sheets

ELECTROCHEMICAL IMMUNOSENSOR AND METHOD OF USE FOR ANALYTE DETECTION

CROSS REFERENCE TO RELATED APPLICATIONS

The instant application claims priority to U.S. Provisional application 62/163,906 filed on 19 May 2015. The U.S. Provisional application 62/163,906 is hereby incorporated by reference in its entireties for all of its teachings.

FIELD OF TECHNOLOGY

The present invention relates to a biosensor and a method of its use for protein detection. More specifically, the present invention relates to an electrochemical immunosensor and a method of its use for protein detection.

BACKGROUND

Electrochemical immunosensor, which is based on antibody-antigen binding, has received widespread recognition and interest due to its cost, simplicity, sensitivity, simple construction and feasibility of miniaturization (Thévenot et al., 1999; Ahmad et al., 2002; Ahmad et al., 2008; Saito et al., 2008; Ahmed et al., 2014). To increase the possibility of antibody-antigen binding and hence the sensitivity of an immunosensor, antibody can be immobilized at a specific site rather than at random orientation. Immunoglobulin, being a glycoprotein, possesses a branched oligosaccharide N-linked to asparagine 297 found in the Fc region. Because oligosaccharide moiety is facing away from the paratope (antigen-binding sites), this sugar moiety can be used for site-specific antibody immobilization without affecting antibody-antigen binding reaction (Sutton & Phillips, 1983). Ho and co-workers (2010) reported a simple method using boronic acid to form reversible cyclic covalent complexes with adjacent 1,2 or 1,3 diols (Springsteen & Wang, 2002) for immobilization of anti-biotin antibodies. However, electrochemical immunosensors cannot measure below a certain limit and thus needs improvement.

SUMMARY

The present disclosure related to an electrochemical immunosensor and its use. More specifically the present disclosure relates to a carbon based electrochemical immunosensor and its method of use.

In one embodiment, the electrochemical immunosensor comprise of at least one sensing electrode in contact with a fluid containing an analyte concentration to be measured. In another embodiment, the electrochemical immunosensor comprise of at least one screen printed electrode (SPE) in contact with a fluid containing an analyte concentration to be measured.

In one embodiment, SPE is a carbon modified SPE whereas in another embodiment, SPE is a CNF modified SPE (CNF-SPE). The electrode has a surface on which a binding agent is present. A portion of the binding agent binds a portion of the analyte within the fluid and forms a complex which is then further detected.

In one embodiment, the CNF-SPE is further functionalized by electrochemical reduction. In another embodiment, CNF-SPE is functionalized by electromagnetic reduction of in situ generated 4-carboxyphenyl diazonium salt in acidic aqueous solution.

In one embodiment, the CNF-SPE is further activated. In another embodiment, the CNF-SPE was functionalized followed by activation by carbodiimide/succinimide (EDC/NHS).

In one embodiment, the CNF-SPE is further fabricated. In another embodiment, the CNF-SPE was fabricated by at least a single layer of 4-aminophenylboronic acid. Fabrication will allow orientation of the binding agent which aid in a complex formation to allow analyte detection.

In one embodiment, the present disclosure relates to a carbon modified SPE wherein the SPE is functionalized by electrochemical reduction, activated by EDC/NHS and fabricated by at least a single layer of 4-aminophenylboronic acid. In another embodiment, In one embodiment, the present disclosure relates to a CNF modified SPE wherein the SPE is functionalized by electrochemical reduction, activated by EDC/NHS and fabricated by at least a single layer of 4-aminophenylboronic acid.

Thus, in one embodiment, the present disclosure relates to an electrochemical immunosensor comprising of at least one electrode wherein the said electrode is a carbon modified electrode; a surface on which a binding agent is present; a fluid to come in contact with the electrode; wherein a portion of the binding agent binds a portion of an analyte within the fluid to form a complex; and an electric signal to be applied to the electrode to generate an ionic response current indicating a level of the analyte in the said fluid. In another embodiment, the present disclosure relates to an electrochemical immunosensor comprising of at least one screen protected electrode wherein the said electrode is functionalized with a carboxyphenyl film followed by activation by EDC/NHS; a surface on which a binding agent is present; a fluid to come in contact with the electrode, wherein a portion of the binding agent binds a portion of an analyte within the fluid to form a complex; and an electric signal to be applied to the electrode to generate an ionic response current indicating a level of the analyte in the said fluid. In some embodiments, the said electrode is further fabricated with at least one layer of 4-aminophenylboronic acid coating.

In one embodiment, the binding agent may be an antibody. In another embodiment, the binding agent may be a ligand, an enzyme or other binding entity capable of forming a complex with the analyte in the said fluid.

In one embodiment, the binding agent may be labeled to aid in detection. In another embodiment, the label may be a fluorescent label, a radiolabeled, luminescent or others as known in the art.

In one embodiment, the present disclosure relates to a method of detecting an analyte concentration using an electrochemical immunosensor is disclosed. In another embodiment, a method of measuring an analyte concentration in a fluid using modified CNF-SPE immunosensor is disclosed. The method as disclosed comprises; providing an electrode wherein the electrode is functionalized by carboxyphenyl film followed by activation by EDC/NHS and fabrication by at least one layer of 4-aminophenyl boronic acid; providing a fluid containing an analyte concentration to be detected; placing the immunosensor in contact with said fluid, wherein the binding agent on the immunosensor comes in close proximity of the analyte in the fluid to form a complex; monitoring an electrical signal developed onto the electrode wherein the signal is dependent upon said number of complex formed; and determining the analyte concentration.

In one embodiment, the method as disclosed comprise of a binding agent onto the surface of modified electrode, wherein the modified electrode is a CNF-SPE electrode. In another embodiment, the method as disclosed comprise of an antibody onto the surface of modified electrode, wherein the modified electrode is a CNF-SPE electrode. In some embodiments, the method as disclosed comprise of a ligand, an enzyme or other binding agent as known in the art onto the surface of modified electrode.

In one embodiment, the method as disclosed comprises of a modified CNF-SPE immunosensor, wherein the immunosensor uses voltametric measurement techniques to convert complex formation responses to a readable electric signal. In another embodiment, the method as disclosed comprises of a modified CNF-SPE immunosensor, wherein the complex formation on the electrode surface is a diffusion controlled electrochemical process.

In one embodiment, the method as disclosed result in highly sensitive detection of an analyte in the said fluid. In another embodiment, the method as disclosed can detect as low as 1 pg/ml of analyte in the said fluid.

In one embodiment, the method as disclosed may be used for detection of a hormone in a fluid whereas in another embodiment, the method may be used to detect levels of recombinant bovine somatotropin (rbST) in a fluid. The method as disclosed can detect hormone level as low as 1 pg/ml.

The above mentioned summary presents a simplified version of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later. Other aspects will be apparent from the following description, figures and the appended claims.

BRIEF DESCRIPTION OF THE DRAWINGS

FIG. 2 (b) differential pulse voltammetry (DPV)s of (A) bare CNF-SPE, (B) 4-carboxybenzenediazonium/APBA/CNF-SPE, (C) 4-carboxybenzenediazonium/APBA/Ab/CNF-SPE, and (D) after formation of complex.

FIG. 3 (b) shows amount of antibody immobilized (%) on carbon, SWCNT- and CNF modified SPE as immobilization platforms (n=3).

FIG. 4 (b) a comparison of the response of the immunosensor to 10 ng/mL of rbST, BSA, hCG and lysozyme (n=3).

FIG. 5 (b) shows a calibration plot showing dependence of the oxidation peak current of square root of scan rate; and FIG. 5 (c) shows a calibration plot showing dependence of the reduction peak current of square root of scan rate.

DETAILED DESCRIPTION

Figure 1:
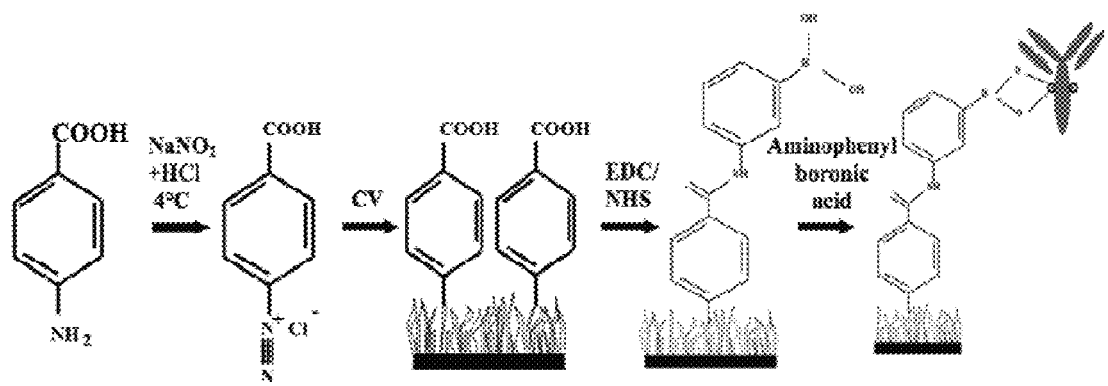
FIG. 1 shows a schematic representation of the fabrication of CNF-SPE electrochemical immunosensor.

In the field of biosensor, undoubtedly nanotechnology plays a significant role in its development towards enhanced signal response and ultimately lower detection limits. Since the discovery of carbon nanotube (CNT) and carbon nanofiber (CNF). Numerous studies were published in literature focusing on their preparation, properties and biosensing applications. CNT can be conceptualized as a sheet of graphene rolled up into a cylindrical tube with diameters ranging from fractions of nanometers to tens of nanometers and lengths from a few micrometers up to several centimeters (Trojanowicz 2006; Dasgupta et al., 2011). Single-walled CNT (SWCNT) comprises of a single layer of graphene forming a cylinder whereas multi-walled CNT (MWCNT) consists of multiple layers of CNT distanced at 0.034 nm apart from each layer (Loos, 2015). CNF comprises of graphene layers that are arranged as stacked cones, cups or plates in cylindrical shape with lengths measured in micrometers and diameters between tens of nanometers up to 200 nm (Vamvakaki et al., 2006). Although the mechanical strength and electric properties are similar to CNT, it is the unique feature of CNF in that the whole surface area can be utilized for antibody immobilization makes CNF an ideal choice for electrochemical immunosensor fabrication. Incorporation of screen-printed electrode (SPE) technology with electrochemical system has paved ways for more applications in the areas of food, environmental, industrial and medical analyses. SPE are preferred due to the advantages of disposability, simplicity and high consistency in analysis performance (Li et al., 2012). Another advantage of SPE was highlighted in a work by Minhaz's group (Lim et al., 2014) that used inert carbon as their counter electrode, instead of platinum usually used in conventional electrode, and acidic solution as their electrolyte. In acidic medium, platinum dissolves into the working solution and this may affect the activity of their system.

Somatotropin, also known as growth hormone, is a peptide hormone synthesized and secreted by anterior pituitary glands of humans and animals that function to stimulate growth and development (Dervilly-Pinel et al., 2014). In dairy cows, somatotropin also enhances milk production and carcass composition but isolation and purification of bovine somatotropin from slaughtered cows was inadequate and not deemed cost-productive for commercial use. In the early 1980s the breakthrough of biotechnology had advanced recombinant DNA technology that resulted in mass production of recombinant bovine somatotropin (rbST). Despite the use of rbST being legal in several countries including USA, many countries (such as the European Union, Canada, Australia) still ban its administration to dairy cows due to concerns regarding the welfare of animals and most importantly safe consumption of milk by human. The primary concern regarding safety of milk being treated by rbST for human consumption is the elevation of hormones such as bovine IGF-1 and its linked to certain tumours. As IGF-1 cannot be destroyed by heat treatment process, the impact it has in human digestive tract still remain unknown (Dervilly- Pinel et al., 2014). This therefore necessitates for a sensitive and reliable detection method to measure levels of rbST and thus to help in reducing misuse of rbST.

In the present invention a simple label-free method for sensitive detection of rbST based on site-directed immobilization of antibodies is disclosed.

The invention further discloses a modified electrode which is a CNF SPE. The electrode was first modified with carboxyphenyl film and then activated by EDC/NHS. A monolayer of 4-aminophenylboronic acid coating was then fabricated onto the electrode to allow orientation of antibody via bonding of boronic acid-saccharide of oligosaccharide moiety located on the Fc region of antibody. The modified electrode is then used for the detection of a hormone such as a rbST in a fluid.

EXPERIMENTAL

Reagents and Materials

Anti-bovine growth hormone (anti-BGH) antibody and recombinant bovine growth hormone (rbST) were purchased from Abcam (USA). Bovine serum albumin (BSA), 1-Ethyl-3-(3-dimethylaminopropyl)carbodiimide hydrochloride (EDC), N-hydroxysuccinimide (NHS), 4-Aminobenzoic acid (ABA), hydrochloric acid, $Na_2HPO_4$, $NaH_2PO_4 2H_2O$ and $KH_2PO_4$, potassium ferrocyanide, potassium ferricyanide, lysozyme, adult bovine serum (Sigma-Aldrich, USA), sodium nitride (Phillips Harris Reagent, UK) 3-aminophenylboronic acid (APBA) (Santa Cruz Biotechnology, USA) and hCG (Abdserotec, UK). All solutions were prepared and diluted using double distilled water throughout this work.

Instrumentation

Electrochemical measurement of cyclic voltammetry (CV) and differential pulse voltammetry (DPV) were analyzed using an Autolab PGSTAT101 III (Metrohm, Netherlands) that works in conjunction with its Nova 1.10 software. The disposable carbon, SWCNT-modified, graphene-modified and CNF-modified carbon working SPE were obtained from DropSens (Spain) that made up of a carbon counter-electrode and silver reference electrode. Nanophotometer P360 (Implen, Germany) was used for UV measurement. All measurements were made at room temperature ($21 \pm 1°$ C.).

Preparation of Aminophenylboronic Electrode (APBA/CNF-SPE)

Aminophenylboronic-modified electrode was prepared based on work by Ho et al., (2010) with slight modification. In an iced water bath, 20 mg of ABA were dissolved in 2 mL of 1 M HCl. 2 mM sodium nitrite aqueous solution was then added in a drop-wise manner with constant stirring to produce the diazonium salt. The solution was allowed to stir for 5 min. Electrochemical functionalization of the working CNF electrode was carried out by placing 40 µL of the solution onto the SPE using one CV cycle ranging between 0.0 and −1.0 V at a scan rate of 200 mV/s. Upon functionalization of SPE, the electrode was rinsed sequentially with distilled water and methanol and dried at room temperature. 10 µL of an EDC/NHS (0.1 M each) solution dissolved in DMSO was dropped onto the modified electrode and allowed to react at room temperature for 1 h. The electrode was washed with distilled water and methanol and then dried. 10 µL of 50 mM APBA was deposited onto the electrode for 3 h producing aminophenylboronic electrode (APBA/CNF-SPE). The resulting modified electrode was washed with distilled water and methanol, and dried before being used for site-specific antibody immobilization.

Site-Directed Immobilization of Anti-BGH Antibody

50 µL of a 10 µg/mL of anti-BGH solution in PBS (10 mM, pH 7.4) was placed onto the APBA/CNF-SPE and incubated overnight at 4° C. The electrode was then washed with PBS solution (10 mM, pH 7.4). To prevent non-specific adsorption, 50 µL of blocking solution (0.1% BSA in PBS solution of pH 7.4) was deposited and left to incubate for 30 min. After 30 min, the antibody-immobilized electrode was rinsed with blank PBS and stored at 4° C. until needed for assay measurement. The fabrication scheme as discussed is depicted in FIG. 1.

Electrochemical Signal Measurement

Different concentrations (from 1 pg/mL to 10 ng/mL) of rbST were prepared in PBS solution (10 mM, pH 7.4). Then, 50 µL of these rbST solutions were placed onto the electrode surface and incubated for 45 min at room temperature. The surface was rinsed thoroughly with blank PBS before DPV measurements were taken in 5 mM $Fe(CN)_6^{3-}/Fe(CN)_6^{4-}$ (10 mM PBS, pH 7.4). The following parameters were used for DPV measurements in this work: potential range −0.4 to +0.5 V, modulation amplitude 25 mV, modulation time 0.05 s, interval time 0.5 s and step potential −5 mV. Difference in the reduction peak of current of the redox mediator $[Fe(CN)]^{3-/4-}$ between blank PBS solution (denoted as $i_0$) and prepared concentration of rbST (denoted as i) was used to monitor the formation of rbST-antibody immunocomplex.

To investigate and compare the differences in sensing performance between different working electrode materials, carbon, SWCNT-modified and graphene-modified SPE were treated exactly using the same protocol as above.

Real Sample Analysis

Analysis in real sample was prepared by firstly diluting bovine serum to 1000-fold with PBS solution (10 mM, pH 7.4). The diluted serum was then spiked with 100 and 200 pg/mL of rbST. 50 µL of the spiked serum was then dropped onto CNF-modified working SPE and allowed to incubate for 45 min at room temperature. The surface was washed thoroughly with blank PBS before DPV measurements were taken in 5 mM $Fe(CN)_6^{3-}/Fe(CN)_6^{4-}$ (10 mM PBS, pH 7.4).

Antibody Immobilization Study on Different Platforms

Adsorption of antibody on carbon, SWCNT-modified and CNF-modified working electrodes was prepared according to Olenic et al., (2009) with modification. 50 µL of rbST solution (100 µg/mL in 10 mM PBS, pH 7.4) was dropped onto the working electrodes and incubated for 30 min at room temperature in moisture-saturated atmosphere. After 30 min, the concentration of antibody solution was determined spectrophotometrically at λ=280 nm. The amount of antibody immobilized on electrode surface was determined by calculating the difference of its concentration before and after immobilization.

Characterization of Aminophenylboronic-Modified Electrode

Figure 2:
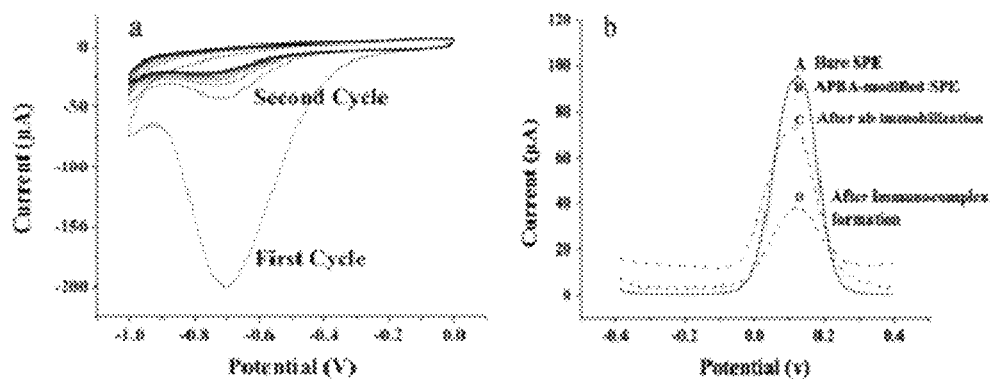
FIG. 2 (a) shows a cyclic voltammetry graphs for the electroreduction of 4-carboxybenzenediazonium ions at a scan rate of 200 mV/s.

Preparation of highly oriented immobilized antibody was performed through a three-step electrografting process of CNF-SPE surface (Ho et al., 2010): 1. Electroreduction of 4-carboxybenzediazonium ion; 2. Activation with NHS/EDC; 3. Derivation with 3-aminophenylboronic acid. Formation of carboxyphenyl film on the electrode surface can be observed that was produced by the CV reduction of the in situ generated carboxyphenyl diazonium salts [FIGS. 2 (a) and 2 (b)]. A monolayer of boronic acid was then produced on the surface of the SPE to immobilize the antibody via their sugar moiety. FIG. 2 (a) presents a wide irreversible reduction peak of diazonium salt on the first scan that gradually diminished on the second and subsequent cycles. This is a typical CV characteristic of formation of organic layer by diazonium salt with the successive disappearance of peaks (Belanger and Pinson, 2011). Each successive CV scan caused each corresponding peak to disappear demonstrating the gradual decrease of electron transfer between diazonium ions in the solution and the electrode surface due to the obstruction of electrode surface by the carboxyphenyl film. Since increasing the number of CV scan resulted in thicker layer of carboxyphenyl film and leading to more blocking of electron transfer, one cycle was selected for electrografting procedure (Eisaa et al., 2013).

Electrochemical Characterization of Immunosensor Fabrication

Characterization of layer by layer immunosensor fabrication accomplished using DPV in 5 mM $Fe(CN)_6^{3-}/Fe(CN)_6^{4-}$ probe in PBS is shown in FIG. 2 (b). As shown in FIG. 2 (b), CV of bare CNF-SPE displayed a prominent cathodic peak of $Fe(CN)_6^{3-}/Fe(CN)_6^{4-}$ at 0.1 V (FIG. 2 (b) A) and after each assembly step had resulted in significant reduction of the $Fe(CN)_6^{3-}/Fe(CN)_6^{4-}$ peak height. Formation of a layer of 4-carboxybenzenediazonium/APBA (FIG. 2 (b) B) caused DPV peak to reduce. Height of DPV peak reduced further upon addition of antibody solution (FIG. 2 (b) C). This reduction of peak height is due to the blocking effect after the formation of subsequent insulating layer that obstructs the process of electron transfer between redox probe and electrode surface. Moreover, the current response decreased significantly further after incubation with antigen rbST hence suggesting the formation of immunocomplex (FIG. 2 (b) D). Immunocomplex formation on the electrode surface served as an electron-transfer and mass-transfer insulating layer as electron transfer was hindered between electron mediator and electrode causing a decrease in signal current response (Yang et al., 2014). Consequently, this became the foundation of our principle for sensitive detection of rbST.

Principle of Voltammetric Process on the Label-Free Immunosensor

Figure 5:
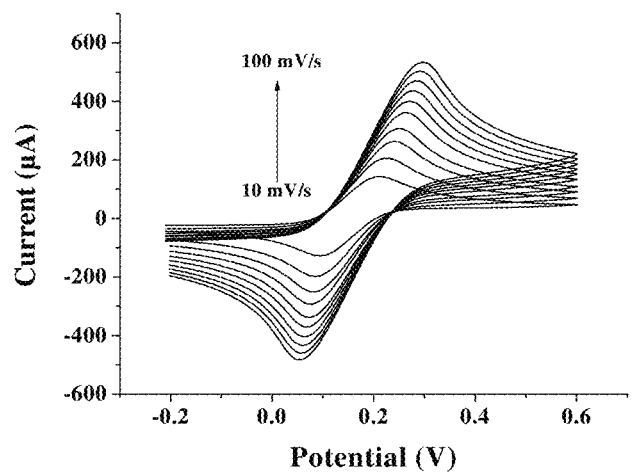
FIG. 5 (a) shows cyclic voltammograms of modified electrodes using different scan rates 10, 20, 30, 40, 50, 60, 70, 80, 90, 100 (from inner to outer cycles) in 10 mM $Fe(CN)_6^{3-}/Fe(CN)_6^{4-}$.
Figure 5:
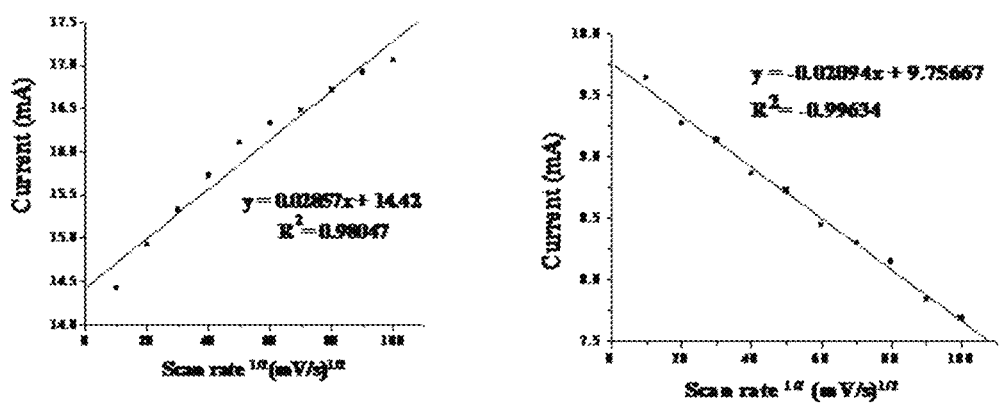

The study of kinetics of the reactions on the electrode surface of our immunosensor was carried out by CV in 10 mM $Fe(CN)_6^{3-}/Fe(CN)_6^{4-}$ in PBS (pH 7.4). The influence of scan rate in the range of 10-200 mV/s was investigated [FIG. 5 (a)] shows anodic and cathodic peak heights increased with increasing scan rates. In addition, anodic and cathodic peak current was plotted against square roots of scan rates showing dependence of the oxidation peak and reduction peak currents of square root of scan rates [FIG. 5 (b) and FIG. 5 (c)] that revealed a linear relationship (correlation coefficients of 0.99634 and 0.98047 respectively). This, in effect, suggested the reaction on the electrode surface of our immunosensor was a diffusion-controlled electrochemical process, which is the ideal characteristic for analytical measurements (Yang et al., 2014).

Optimization of Electrochemical Immunosensor

Figure 3:
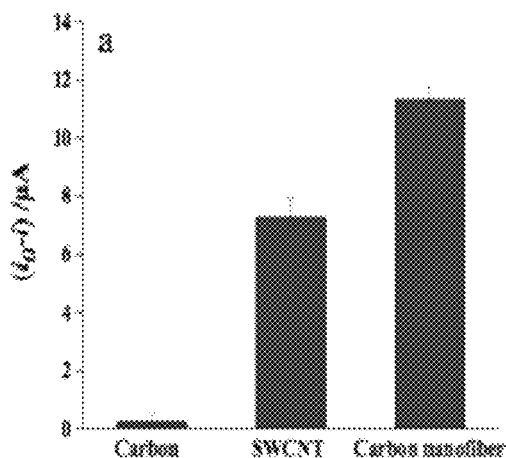
FIG. 3 (a) shows a comparison between different working electrode materials of carbon, SWCNT-modified and CNF-modified SPE for the detection of rBST at 10 ng/mL.
Figure 3:
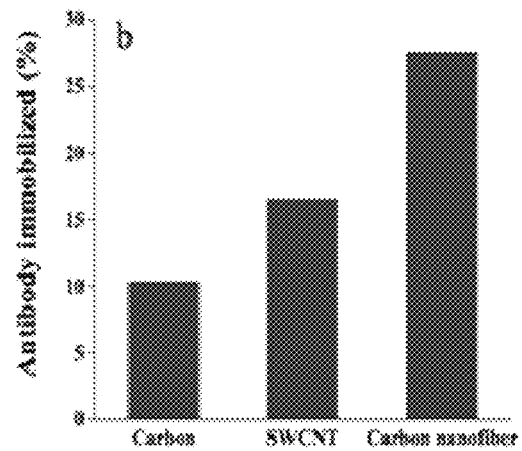

A comparison study between different electrode materials was carried out to determine which material gave the highest performance to our immunosensor construction. Highest current change ($i_0-i$) was observed when CNF was used as the transducer for the detection of rbST at 10 ng/mL [FIG. 3 (a)]. Vamvakki and his group (2006) also compared the analytical performances of CNF-, SWCNT- and graphite-based glucose biosensors with the CNF possessing a much higher sensitivity and this was in agreement with our result. They demonstrated CNF provided the best immobilization support for enzymes and protein amongst the three materials investigated. According to their report, the superior characteristic of CNF can be attributed principally to its unique structure in which its whole surface area can be activated, an ideal case for the immobilization and stabilization of biomaterials (Vamvakki et al., 2006). The physical characteristic of CNF was studied and examined in detail by Kim and Lee (2004). Their high-resolution transmission electron microscopy image revealed CNF comprises many edge sites, to facilitate electron transfer, on its surface as evidence by the inclined graphite basal layers to the fiber growth axis. We also investigated the immobilization capacity of biomolecules onto carbon, SWCNT- and CNF-modified SPE as shown in FIG. 3 (b). Our result indicated that CNF immobilized the highest amount of antibody as determined by UV spectroscopy at $\lambda=280$ nm and calculated from the difference of antibody concentration before and after immobilization. Consistent with the findings of our work, Baker et al. (2006) also reported CNF to show approximately 10 times higher activity compared to the modified glassy carbon surfaces for the detection of cytochrome c. It is essential to point out that comparison with graphene-modified SPE was not possible to perform in this study due to the detachment of the working electrode film from the electrode strip during preparation step.

Figure 6:
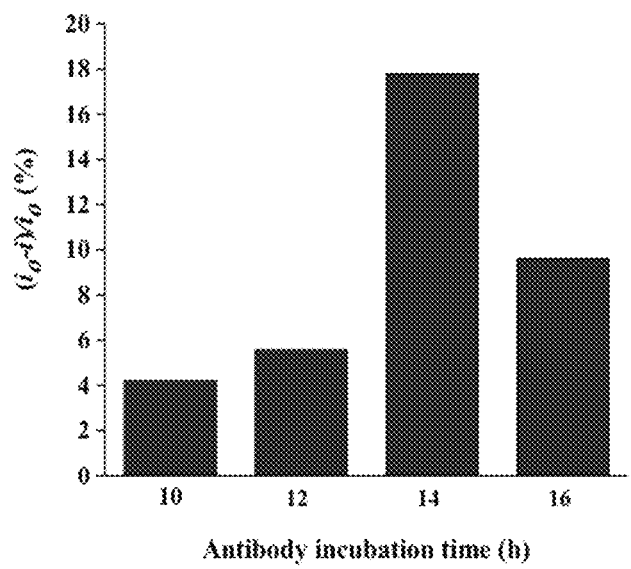
FIG. 6 shows graph of antibody incubation time-response at 4° C. of 1 ng/mL rbST based on the difference of the DPV peak currents.
Figure 7:
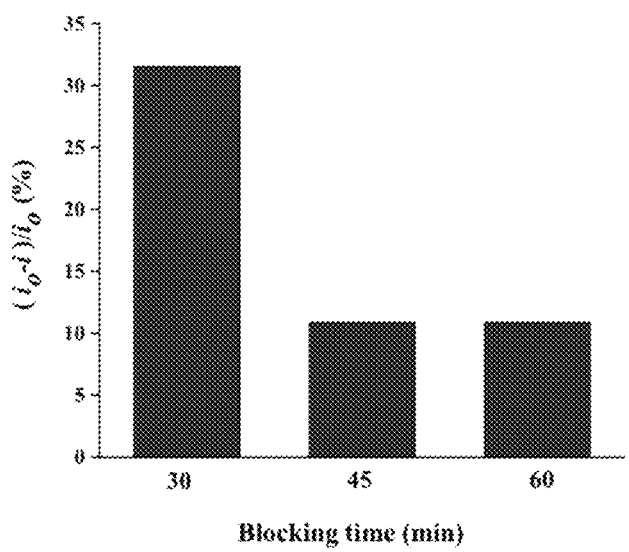
FIG. 7 shows response of the immunosensor to 1 ng/mL rbST based on the relative change of the DPV peak currents with blocking time assigned at 30, 45 and 60 min.
Figure 8:
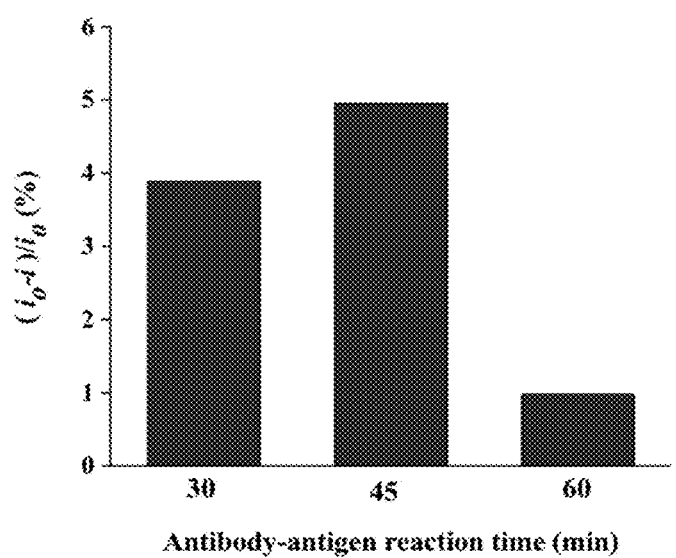
FIG. 8 shows antibody-antigen-reaction time of rbST at 1 ng/mL based on relative current change of DPV peaks.

Several experimental parameters were investigated in this work to ensure maximum analytical response of our immunosensor. The influence of blocking time, antibody-antigen reaction time and antibody incubation time was examined. It was found that maximum current change took place when antibody was incubated for 14 hours. Incubation more than 14 hours decreased the current change and this indicated a maximum antibody immobilization had occurred (FIG. 6). The blocking time is another important parameter studied to reduce the effect of non-specific binding, in which the blocking time was assigned for 30, 45 and 60 min. The maximum current change was observed when the electrode was blocked for 30 min at room temperature (FIG. 7). The effect of immunocomplex formation time on the current response evaluated in this study showed antibody-antigen formation reached its peak at 45 min when 1 ng/mL of rbST was used and this time was assigned as the incubation time for immunocomplex formation (FIG. 8).

Analytical Performance of the Immunosensor

The determination of rbST relied on the reduction of DPV current after the binding of antibody and rbST. With higher concentration of antigen rbST, higher change of peak current was observed since the formation of more immunocomplexes caused thicker layer and this further impeded electron transfer between $Fe(CN)_6^{3-}/Fe(CN)_6^{4-}$ redox probe and electrode surface. In order to demonstrate the relationship between the change of the cathodic peak current of redox probe in response to antibody-antigen binding event, a calibration plot versus the logarithm of different concentrations of rbST was plotted [FIG. 4 (a)]. Under optimal experimental conditions, a linear relationship from 1 pg/mL to 10 ng/mL (correlation coefficient of 0.9721) and detection limit of 1 pg/mL were achieved for rbST detection. Our limit of detection was obtained by visual evaluation, which is the amount of rbST that can be truly be detected in solution (Shrivastava and Gupta, 2011). The low detection limit acquired in this work is postulated due to the high surface area, high surface-active groups-to-volume ratio and thus their outstanding ability for protein immobilization and stabilization, together with their excellent electron mediation characteristics (Vamvakaki and Chaniotakis, 2007). The presence of more edge plane defects on the outer wall of CNF due to stacking of graphene sheets of various shapes may facilitate electron transfer of electroactive species (Vamvakaki and Chaniotakis, 2007). rbST also possesses an isoelectric point of 8.26 which in effect acquires a positive charge at pH 7.4 of $Fe(CN)_6^{3-}/Fe(CN)_6^{4-}$ solution that results in attracting $Fe(CN)_6^{3-}/Fe(CN)_6^{4-}$ anions and contributes to better sensitivity (Eissa et al., 2013).

Application of the Immunosensor in Serum

TABLE 1

Determination of rbST in spiked bovine serum (n = 3).

| Concentration (pg/mL) | Actual detected (pg/mL) | Recovery % | RSD % |
|---|---|---|---|
| 200 | 217.7 | 108.866 | 6.87331 |
| 100 | 81.3 | 81.26611777 | 7.35118 |

Determination of rbST for real sample analysis was performed by spiking 100 pg/mL and 200 pg/mL of antigen rbST in bovine serum. From Table 1, recoveries for these two samples of 100 and 200 pg/mL were 81.27% and 108.87% respectively.

Table 2 displays different immunoassay protocols used to determine rbST. Comparison with published LOD of various immunoassays in the literature showed that our proposed immunosensor gives the lowest limit of detection for rbST. In addition, detection by ELISA (USCN Life Science Inc.) protocol reported a low detection limit of 125 pg/mL by manufacturer.

TABLE 2

Comparison of performances of different immunoassay for the determination of rbST.

| Techniques | LOD | Reference |
|---|---|---|
| Surface plasmon resonance immunosensor | 8 ng/mL | Heutmekers et al., (2007) |
| Electrochemiluminescent immunoassay | 5 pg/mL | McGrath et al., (2008) |
| Localized surface plasmon resonance immunosensor | 3.7 ng/mL | Sadabadi et al., (2013) |
| Electrochemical immunosensor | 1 pg/mL | As disclosed in the present application |

Selectivity of the Immunosensor

Figure 4:
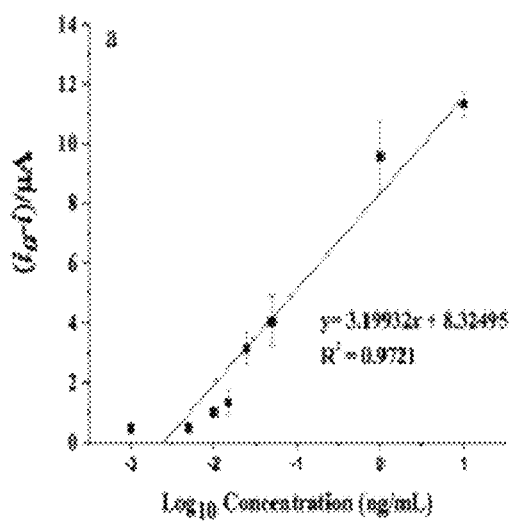
FIG. 4 (a) shows calibration plot of DPV peak current change of concentration from 1 pg/mL to 10 ng/mL.
Figure 4:
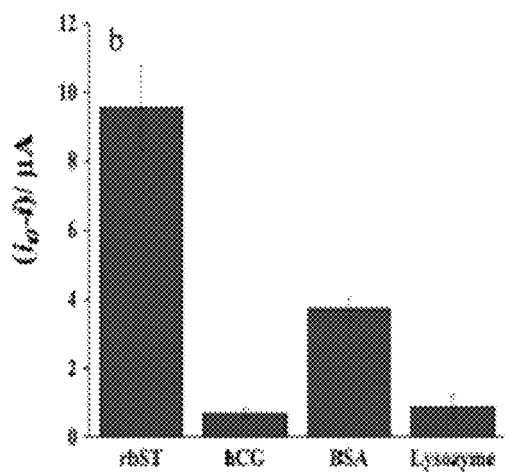

To study the selectivity of the electrochemical immunosensor, 10 ng/mL of human chorionic gonadotropin (hCG), BSA and lysozyme were employed as antigens. The signals were compared and as depicted in FIG. 4 (b), a significantly higher current drop was observed with the target rbST than with other non-target proteins, which indicated our immunosensor exhibited excellent selectivity for the detection of rbST.

The study demonstrates a label free immunosensor system is simple and exhibited an excellent sensitivity and selectivity without the need of multiple signal amplification steps. The results show that carbon nanofiber gave higher electrochemical signal response than when SWCNT was used as an electrode. This can be attributed to the unique characteristic of carbon nanofiber that provides a better antibody immobilization support than SWCNT. The strategy presents a straightforward approach for future development of rapid and portable integrated device for on-site hormone detection for food safety analysis.

What is claimed is:

1. A method of detecting an analyte in a fluid, comprising:
   providing an electrochemical immunosensor comprising an electrode wherein the electrode is functionalized by electrochemical reduction using carboxyphenyl, and activated by carbodiimide/succinimide; wherein the electrode being a modified carbon nano-fiber-based electrode;
   providing a fluid containing an analyte concentration to be detected;
   placing the immunosensor in contact with said fluid, wherein a binding agent on the immunosensor comes in close proximity of the analyte in the fluid to form a complex;
   monitoring an electrical signal developed onto the electrode wherein the signal is dependent upon said number of complex formed; and
   determining the analyte concentration.

2. The method of claim 1, wherein the analyte is a recombinant bovine somatotropin.

3. The method of claim 1, wherein the binding agent is an antibody.

4. The method of claim 1, wherein the electrode is further fabricated with at least one layer of 4-aminophenylboronic acid coating.

5. The method of claim 1, wherein the electrode is a screen printed electrode.

6. The method of claim 5, wherein the screen printed electrode is a carbon nano-fiber screen printed electrode.

7. The method of claim 1, wherein the analyte is a protein.

8. The method of claim 3, wherein an antibody forms a complex with the analyte to be determined within the said fluid.

9. The method of claim 1, wherein the binding agent is a binding entity capable of forming a complex with the analyte in the said fluid.

* * * * *